United States Patent [19]

Huene

[11] 3,985,129

[45] Oct. 12, 1976

[54] DEVICE FOR USE IN PROTECTING A PATIENT DURING REMOVAL OF AN IMMOBILIZING CAST

[76] Inventor: Donald R. Huene, 7429 N. Valentine, Fresno, Calif. 93705

[22] Filed: Jan. 29, 1975

[21] Appl. No.: 545,127

[52] U.S. Cl. ............................... 128/91 A; 30/289
[51] Int. Cl.² ......................................... A61F 15/02
[58] Field of Search ............. 128/91 A, 83; 30/166, 30/370, 290, 292, 296, 286, 289

[56] References Cited
UNITED STATES PATENTS

| | | | |
|---|---|---|---|
| 1,716,662 | 6/1929 | Pedley | 30/370 |
| 2,070,358 | 2/1937 | Hengstenberg | 30/370 |
| 2,146,916 | 2/1939 | Richards | 30/289 |
| 2,187,175 | 1/1940 | Prosperi | 128/91 A |
| 2,523,837 | 9/1950 | Luger | 128/91 A |
| 2,571,527 | 10/1951 | Boyer | 30/292 |
| 2,837,088 | 6/1958 | Moses | 128/91 A |
| 3,353,266 | 11/1967 | Goolsby | 30/370 |

*Primary Examiner*—John D. Yasko
*Attorney, Agent, or Firm*—Huebner & Worrel

[57] ABSTRACT

A device for protecting a patient during removal of an immobilizing cast. The device is of a U-shaped configuration and includes an elongated planar shield and an elongated planar guide connected with the shield, at one end thereof and disposed in superimposed parallelism with the shield, whereby the shield is adapted to be inserted between the adjacent surfaces of the skin of a patient and a cast to be removed, and employed for both guiding a cutter along the external surface of the cast and shielding the patient from the cutter as it is caused to penetrate the cast.

1 Claim, 5 Drawing Figures

DEVICE FOR USE IN PROTECTING A PATIENT DURING REMOVAL OF AN IMMOBILIZING CAST

BACKGROUND OF THE INVENTION

The invention generally relates to shields for use in the medical profession, and more particularly to a device for use in protecting a patient during the removal of an immobilizing cast, hereinafter referred to simply as a cast, employing a cutting device such as a cast saw having a circular blade.

As can readily be appreciated by those familiar with the use of cast saws in the removal of casts such as those formed from plaster of paris, a cast saw includes a circular blade having peripheral teeth which serve to form a kerf as oscillatory motion is imparted thereto. Unfortunately, the skin of a patient often times is subjected to injury as a consequence of a saw blade inadvertently penetrating too deeply into the cast being removed.

Attempts to avoid such injury have lead to the use of a simple ruler being inserted between a cast to be removed and the skin of a patient for thus protecting the patient's skin from the saw blade being used for cutting the cast. While this technique has been successfully employed on many occasions, it has been found that there is a distinct tendency for the saw blade to move off the ruler and thus injure the patient. This results, usually, from a lack of an ability to visually observe the position of the inserted ruler, as well as from an inability to form a straight kerf. Consequently, the removal of casts remains a difficult and time-consuming task.

Therefore, while devices such as rulers and the like have been employed with varying degrees of success, it should be apparent that there still exists a need for a practical and economic device which can be readily employed for expediting the removal of casts, using cast saws, without subjecting patients to injury.

It is, therefore, the general purpose of the instant invention to provide a practical, simple, and economic device which can readily be employed in successfully shielding patients during the removal of casts, whereby cast-removal operations may be expedited while simultaneously reducing the likelihood that patients will suffer saw-induced injury.

OBJECTS AND SUMMARY OF THE INVENTION

It is, therefore, an object of the instant invention to provide a device which overcomes the aforementioned difficulties and disadvantages.

It is another object to provide a device for protecting a patient during removal of an orthopedic cast.

Another object is to provide a device which is particularly useful in removing orthopedic casts from a limb of a patient, although not necessarily restricted thereto since it may be employed in removing casts from trunks, as well as limbs.

It is another object to provide a device which includes a shield adapted to be inserted into a cast into protective relationship with a patient's skin and a guide adapted to extend along the external surface of the cast for guiding a cast saw.

Another object is to provide a practical, economic, and readily employable device for use in protecting a patient from a cast saw including a shield adapted to be inserted into a protective relationship with the skin of a patient and yet provide a visually observable saw guide extended along the surface of the cast for maintaining a saw in proper relation with the shield as the saw is operated for cutting the cast.

These and other objects and advantages are achieved through the use of a device which includes an elongated flexible body of a substantially U-shaped configuration, including an elongated planar shield adapted to be inserted between the skin of a patient and a cast to be removed, and an elongated planar guide connected with the shield at one end thereof and disposed in superimposed parallelism with the shield, as will become more readily apparent by reference to the following description and claims in light of the accompanying drawings.

DESCRIPTION OF THE PREFERRED EMBODIMENT

Figure 1:
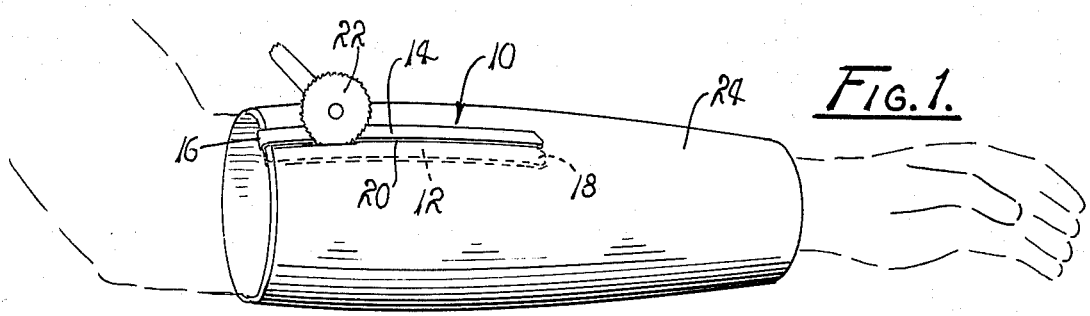
FIG. 1 is a pictorial view illustrating one manner in which the device of the instant invention is employed.

Referring now to the drawings wherein like reference characters designate like or corresponding parts throughout the several views, there is shown in FIG. 1 a device, generally designated 10, which embodies the principles of the instant invention.

Figure 2:
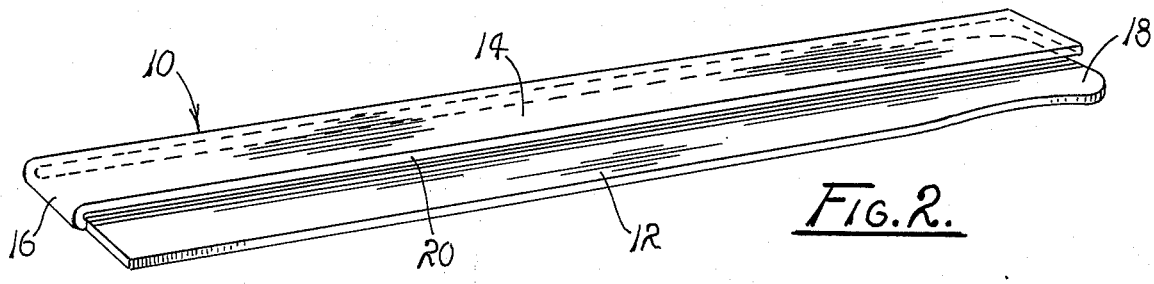
FIG. 2 is a perspective view of the device.
Figure 3:
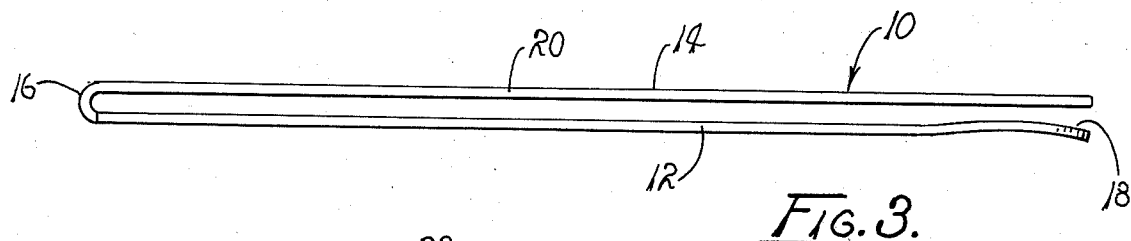
FIG. 3 is a side elevation of the device.
Figure 4:
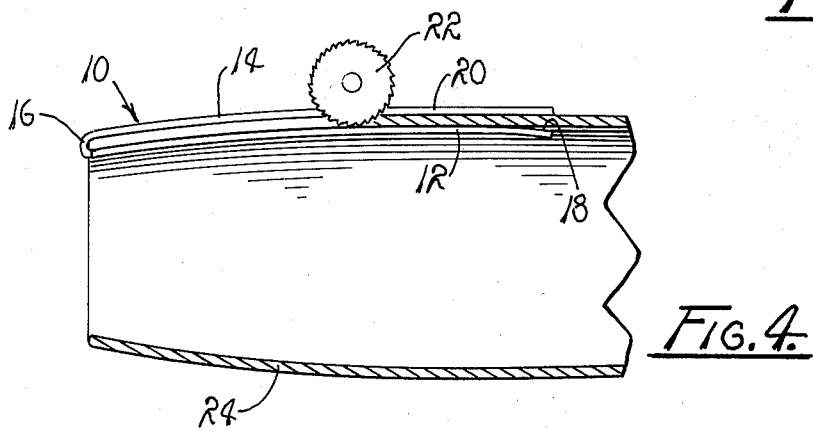
FIGS. 4 and 5 are cross-sectional views which, when taken collectively, further illustrate the manner in which the device of the instant invention is employed.
Figure 5:
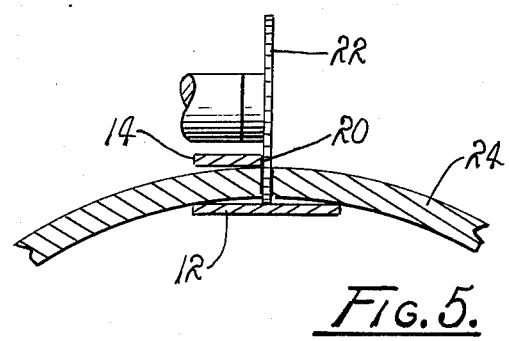

As best shown in FIGS. 2 and 3, the device 10 comprises an integral body which includes a shield 12 of an elongated planar configuration and a guide 14 interconnected with the shield 12 through an arcuate end segment 16. Where so desired, the device 10 is fabricated from suitable synthetic resins such as polyvinyl chloride having adequate hardness for protecting a patient, while possessing sufficient flexibility to permit the shield 12 to be inserted between the skin of a patient and a cast to be removed. It will, of course, be appreciated that the device can be fabricated from suitable metals.

The end surface 18 of the shield 12, opposite the arcuate end segment 16, preferably is curved in normally related planes for facilitating an insertion of the shield 12 between the cast to be removed and the skin of the patient, without encountering obstruction through an engagement with either the cast or the skin of the patient.

Furthermore, the guide 14 includes a guide surface 20 of a linear configuration which extends the length thereof. This surface lies in a reference plane coincident with the longitudinal plane of symmetry of the device 10. Consequently, by causing a saw, indicated by the reference numeral 22, to be maintained in engagement with the guide surface 20, as a kerf is formed in the cast, for facilitating the removal thereof, the shield 12 always remains interposed between the saw blade and the skin of the patient from whom the cast is being removed.

Moreover, it is to be understood that the length of the device 10 will be varied as desired. For example, a device 10 having a length slightly greater than one-half the length of the cast to be removed may be found to be entirely suitable, while, in some instances, the device 10 should exceed the length of the cast.

In order to employ the device 10 of the instant invention, the shield 12 is inserted, at one end of a selected cast, such as a cast designated 24, between the adjacent surfaces of the cast and the patient's skin. Insertion of the shield is facilitated through the configuration of the end surface 18 which is suitably curved for enhancing insertion.

As the shield 12 is inserted between the cast and the skin of the patient, the guide 14 is extended along the external surface of the cast in a superimposed relationship with the shield. Once the shield is properly located beneath a proposed line of cut for a saw, such as a saw blade 22, the blade 22 is positioned against the guide surface 20 and caused to oscillate for cutting the cast in a manner well understood. As the saw blade penetrates the cast it engages the surface of the shield 12. Thus, the saw blade is positioned to be moved in a substantially straight line extended along a path defined by the guide surface 20. So long as the saw blade remains in engagement with the guide surface 20, the shield 12 remains interposed between the saw blade and the skin of the patient for thus protecting the patient. Deviation from a proposed line of cut, therefore, can readily be observed. Where the relative lengths of the device 10 and cast 24 are such as to render it desirable to cut from opposite ends of the cast, the shield 12 is extracted and again inserted, in an opposite direction, between the cast and skin of the patient with removal operations being thereafter resumed for purposes of completing the removal of the cast.

While the device of the instant invention has particular utility in protecting a patient from the effects of an oscillating cast saw, it is to be understood that the device also may be employed with other types of cast cutting devices including shears and the like.

In view of the foregoing, it should readily be apparent that the device of the instant invention provides a practical, economic and readily employable shield for use in cutting casts from limbs of patients.

Although the invention has been herein shown and described in what in conceived to be the most practical and preferred embodiment, it is recognized that departures may be made therefrom within the scope of the invention, which is not to be limited to the illustrative details disclosed.

Having described my invention, what I claim as new and desire to secure by Letters Patent is:

1. A device for use in cast removal procedures for removing a cast from a patient, comprising an elongated, substantially flexible body of a substantially U-shaped configuration including:

A. an elongated shield of a substantially planar configuration having length dimension equal to at least one-half the length dimension of a cast to be removed from a patient, a width dimension substantially greater than the width dimension of a kerf to be formed by a saw adapted to be employed in cutting the case, and a thickness dimension less than the distance between the surface of the skin of a patient and the opposed surface of the cast to be removed from the patient, and an end surface of a compound curve configuration for facilitating insertion of the shield between the skin of a patient and the cast to be removed, whereby the shield is adapted to be inserted between the skin of a patient and the cast to be removed; and B. a cutter guide arranged in superimposed parallelism with the shield and integrally connected by a coupling segment of an arcuate configuration to the opposite end thereof having a length dimension substantially equal to the length dimension of the shield and a width dimension equal to one-half the width dimension of the shield, and including at least one straight edge surface extended the length of the guide in coinciding relation with the longitudinal plane of symmetry passing through said shield, along the length thereof, whereby the guide is adapted to be extended along the external surface of the cast to be removed for guiding a saw along the surface of the shield as the saw forms a kerf on the cast.

* * * * *